United States Patent
Choate

[19]
[11] Patent Number: 5,897,195
[45] Date of Patent: Apr. 27, 1999

[54] OBLIQUE LED ILLUMINATOR DEVICE

[75] Inventor: Albert G. Choate, Rush, N.Y.

[73] Assignee: Optical Gaging, Products, Inc., Rochester, N.Y.

[21] Appl. No.: 08/987,049

[22] Filed: Dec. 9, 1997

[51] Int. Cl.$^6$ ............................................. F21V 5/00
[52] U.S. Cl. ........................... 362/33; 362/246; 362/800
[58] Field of Search ............................. 362/33, 240, 244,
362/246, 252, 335, 336, 338, 800, 804;
359/355, 387; 356/237.1, 237.2

[56] References Cited

U.S. PATENT DOCUMENTS

| | | | |
|---|---|---|---|
| 4,893,223 | 1/1990 | Arnold | 362/800 |
| 5,690,417 | 11/1997 | Polidor et al. | 362/244 |

Primary Examiner—Y. Quach
Attorney, Agent, or Firm—Shlesinger, Fitzsimmons & Shlesinger

[57] ABSTRACT

The illuminator has a cylindrical or truncated-conical array of LEd's producing collimated light beams that are directed onto axially-spaced, inclined surfaces formed on the outer periphery of a hollow, similarly shaped (i.e., cylindrical or truncated-conically shaped) Fresnel-like diffuser which refracts and directs rings of light beams onto the surface of a workpiece at angles of incidence ranging anywhere from 15° to 80°. The array of LED's surrounds the associated Fresnel-like diffuser coaxially thereof, and in turn is surrounded by a circuit board which supplies power selectively to illuminate LED's in the array thereof. The Fresnel-like diffusers have in the outer peripheral surfaces thereof circumferential grooves forming on their outer surfaces annular, prism-shaped projections which differ in shape depending upon the desired angle of incidence of the light beams that are to be projected thereby onto a workpiece.

13 Claims, 2 Drawing Sheets

OBLIQUE LED ILLUMINATOR DEVICE

BACKGROUND OF THE INVENTION

This invention relates to surface illuminators, and more particularly to an improved such illuminator which employs LED light sources that are arrayed in a novel manner. More particularly this invention relates to an improved LED surface illuminator employing novel Fresnel-like diffuser elements which provide illumination at higher angles of incidence than was previously possible with known, prior art illuminators.

It has been customary in many, known illuminators to employ light emitting diodes (LED's) for producing a variety of light sources for illuminating a workpiece. See for example U.S. Pat. No. 4,893,223 and No. 5,038,258. More recently U.S. Pat. No. 5,690,417, which is owned by the assignee of the present application, discloses the use of LED's in surface illuminators along with an associated Fresnel lens for redirecting light from LED lamps toward a workpiece that is to be inspected. In that patent, the LED's are arrayed in coaxially disposed, radially spaced arrays with the light emitting ends of the LED's disposed in a common plane, and with a light beams emitted thereby being directed along spaced, parallel axes. The associated Fresnel lens redirects the beams angularly towards a workpiece. Such an apparatus is capable of providing illumination at angles of incidence at a range having a maximum of approximately 45°.

It is an object of this invention, therefore, to provide an improved surface illuminator which utilizes LED lamps for providing illumination, but which also has the capability of providing illumination at higher angles of incidence then was heretofore possible.

Still another object of this invention is to provide an improved surface illuminator which utilizes LED lamps and associated, flexible circuit boards which enable the lamps to be arrayed selectively in cylindrical or conical arrays.

A more specific object of this invention is to provide an improved LED illuminator of the type described, which employs in combination with the LED light sources, modified or hybrid Fresnel-type diffusers which enable light beams to be refracted and directed onto a workpiece at angles of incidence ranging between 15° to 80°.

Other objects of the invention will be apparent hereinafter from the specification and from the recital of the appended claims, particularly when read in conjunction with the accompanying drawings.

SUMMARY OF THE INVENTION

An LED illuminator of otherwise conventional design is provided with a cylindrical or truncated-conical array of LED light sources or lamps producing collimated light beams that are directed onto the grooves formed in similarly shaped (i.e., cylindrical or truncated-conically shaped) Fresnel-type diffusers which refract and direct light beams onto the surface of a workpiece at angles of incidence ranging anywhere from 15° to 80°. The array of LED's (cylindrical or truncated-conical) surrounds the associated Fresnel-type diffuser coaxially thereof, and in turn is surrounded by a circuit board which supplies power selectively to illuminate LED's in the array thereof.

In order to provide beams directed at various angles of incidence onto a workpiece, the Fresnel-like diffusers have formed in the outer peripheral surfaces thereof a plurality of axially spaced, circumferential grooves, which for the most part are generally triangular in cross section, thus forming on the outer surface of the diffuser annular, prism-shaped projections. As in a conventional Fresnel lens, the prism-shaped projections are not identical, but differ in shape dependent upon the desired angle of incidence of the light beams projected thereby onto the workpiece that is to be inspected.

THE DRAWINGS

Figure 2:
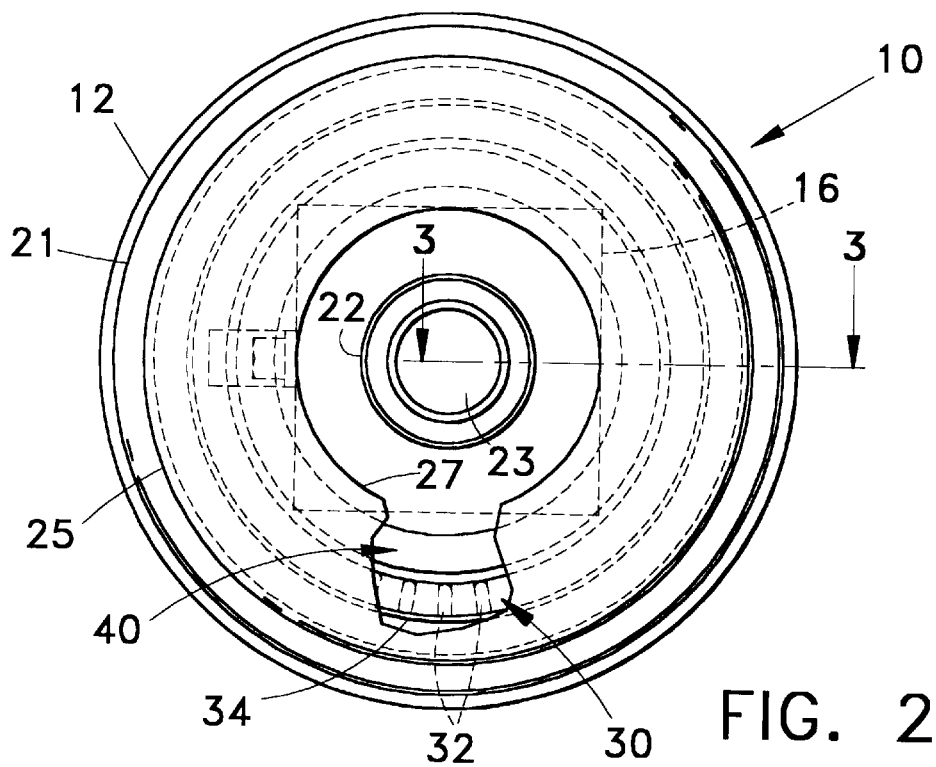
FIG. 2 is a bottom plan view of this illuminator with a portion of the housing broken away.
Figure 3:
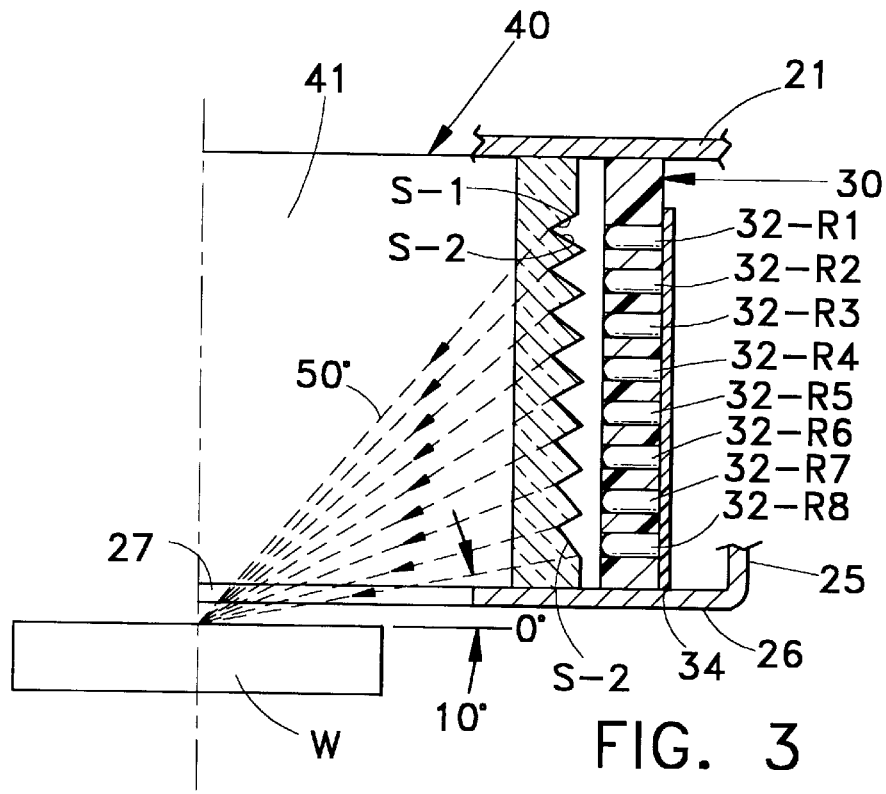
Figure 4:
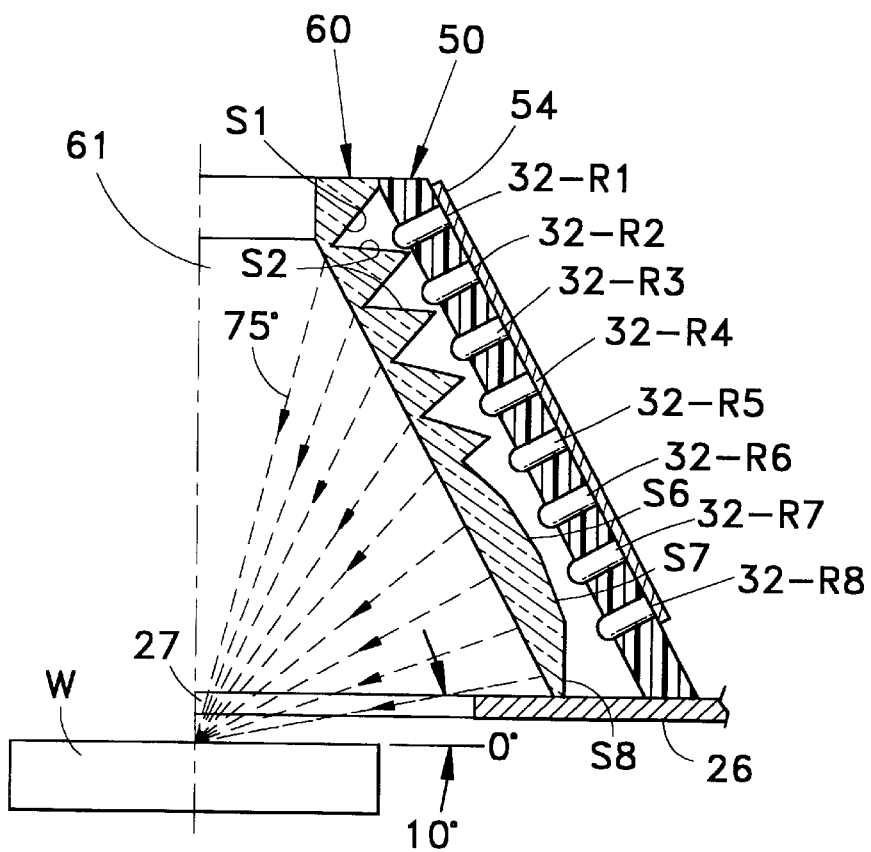

FIG. 3 is a fragmentary sectional view taken generally along the line 3—3 in FIG. 2 looking in the direction of the arrows, and illustrating in greater detail the Fresnel-like diffuser employed in this invention to direct beams of light from the associated LED lamps onto a workpiece; and FIG. 4 is a fragmentary sectional view generally similar to that shown in FIG. 3, but illustrating a different form of the Fresnel-like diffuser and the LED lamps associated therewith.

DETAILED DESCRIPTION OF THE PREFERRED EMBODIMENTS

Referring now to the embodiment shown in FIGS. 1 to 3, 10 denotes generally a surface illuminator comprising an upper, inverted, generally cup-shaped housing 12 having in its upper, closed end a central, circular opening 14. Opening 14 registers with the entrance lens 15 of a conventional optical system assembly contained in a housing 16 that is secured by a bracket 17 and nut 18 on the upper surface of housing 12. As noted in greater detail hereinafter, the optical system in the housing 16 is disposed to receive and produce the image of a workpiece W which is mounted on a conventional support S beneath the illuminator 10.

Mounted coaxially at its upper end in the lower end of the upper housing 12 is a lower housing 21. Secured in and projecting from the bottom of lower housing 21 coaxially thereof is a conventional image generating optical system 22 including an imaging lens 23, which is surrounded adjacent its upper end by a conventional, fiber optics illuminator 24. The image produced by lens 23 is transmitted to the optical system in housing 16 by conventional means which form no part of this invention. Secured at its upper, open end to the underside of housing 21 coaxially thereof, and extending downwardly beneath housing 21 is a large, generally cup-shaped, metal housing or cover 25. Cover 25 has in its lower, closed end 26 a large circular opening 27 which is disposed coaxially of the lens system 22, and is positioned above and in registry with the workpiece W mounted on the support S.

Secured to and projecting from the underside of housing 21 coaxially thereof, and into cover 25 radially outwardly of opening 27 is an annular lamp housing that is denoted generally by the numeral 30. In the embodiment illustrated, the annular wall forming housing 30 has therethrough three-hundred-eighty-four radial openings arranged in eight axially spaced rings, there being forty-eight equi-spaced openings per ring, and with the axial centerlines of all openings in each ring extending radially of the axial centerline of housing 30 and lying in a common plane extending normal to the centerline of housing 30. Secured coaxially in each of the above-noted radial openings in housing 30 is a conventional light emitting diode (LED), each of which lamps is denoted in the drawings by the numeral 32, since the LED's are identical. However, simply to help identify the eight rings of LED lamps employed in this embodiment, the eight, vertically spaced lamps shown in FIG. 3 have been followed by the numerical subscripts RI through R8 to indicate that the lamps 32 in the ring remote from workpiece W lie in ring R1, while the lamps in the ring closest to the workpiece W lie in ring R8.

The ends of lamps 32 remote from their light emitting ends project slightly out of the outer ends of their associated recesses in the housing 30, and into engagement with the face of an annular, printed circuit board 34, which surrounds and is secured to the outer peripheral surface of housing 30 between the bottom of housing 21 and the bottom 26 of the cover 25. Each of the light emitting diodes 32 has its light emitting end facing the axial centerline of housing 21 and cover 25, and has secured thereover a collimating lens which functions to direct collimated light from the associated LED 32 radially of the centerline of cover 25, and parallel to the beams emitted by the other LED's.

Secured to and extending coaxially between the housing 21 and the closed end of cover 25 radially inwardly of the lamp supporting housing 30 is an annular Fresnel-like diffuser element denoted generally by the numeral 40. Diffuser 40, which may be made of glass or a plastic material, has therethrough an axial bore which is disposed coaxially of cover 25 and the imaging lens system 22, and which forms in element 40 a smooth inner peripheral surface 41. On the other hand, the outer peripheral surface of element 40 has formed therein eight, axially-spaced circumferential grooves, each of which grooves is defined by two intersecting surfaces S1 and S2, the former of which is inclined upwardly from a plane extending through the intersection of the surfaces and normal to the axis of the diffuser element 40, and the latter of which is inclined downwardly from such plane. In FIG. 3 only the two intersecting surfaces S1 and S2 of the uppermost groove in element 40 (the groove remote from the workpiece W and immediately adjacent to the underside of the housing 21) has its two intersecting surfaces identified as S1 and S2, respectively, but it will be understood that the two intersecting surfaces of each of the remaining seven grooves likewise have one surface thereof (S1) inclined upwardly from an intersecting plane extending normal to the axis of member 40, and the other surface thereof (S2) being inclined downwardly from the associated intersecting plane. Also as shown in FIG. 3, the light emitting ends of the LED's 32 in each of the eight rings register with and direct collimated light onto one of the eight downwardly inclined surfaces S2 formed on the outer peripheral surface of element 40. In other words, each of the rings R1 through R8 of lamps 32 registers with one of the eight, downwardly inclined surfaces S2 formed on the outer periphery of diffuser 40.

Diffuser 40 functions similar to a conventional Fresnel lens to refract light, in that the separate light beams are deflected toward a common focus. For example, as shown more clearly in FIG. 3, the angle at which a respective surface S2 is inclined downwardly from the associated intersecting plane, increases from a minimum value for the angular inclination of the uppermost surface S2 which registers with ring R1, to a maximum angle of inclination for the lowermost surface S2 as shown in FIG. 3—i.e., the surface S2 immediately adjacent to the bottom wall 26 of the cover 25 and in registry with ring R8. The result is that the angle of incidence at which the beams of light from the LED's 32 in a respective ring strike the registering surface S2 on element 40 thereof differs for each of rings R1 through R8. And in turn, the angle at which the light beams of each ring is refracted likewise differs from ring to ring, and as shown by the beams represented by broken lines in FIG. 3, the angle of refraction decreases from a maximum for the beams of ring R1 to a minimum for those of ring R8.

Figure 1:
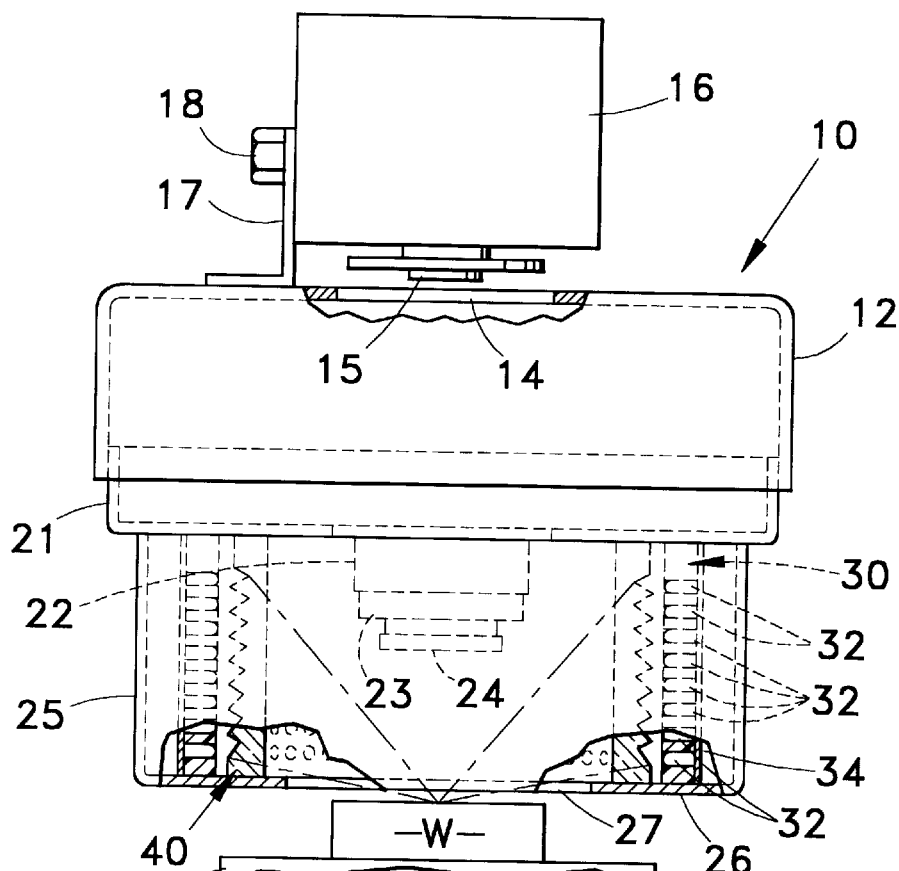
FIG. 1 is a fragmentary side elevational view of a surface illuminator and workpiece support made according to one embodiment of this invention, portions of the illuminator housing being broken away and shown in section for purposes of illustration.

The advantage of employing an annular array of LED's in combination with an annular diffuser element of the type denoted in 40 in FIGS. 1 to 3, is that it is thus possible to direct light onto the workpiece W at substantially higher angles of incidence than was previously made possible with prior, known surface illuminators. As shown for example in FIG. 3, the first embodiment of this invention, which utilizes a cylindrical array of LED's 32 in combination with the cylindrical diffuser element 40, enables the projection of beams of light onto the workpiece at an angle of incidence as low as approximately 40°, and upwardly to a maximum of approximately 80°. Each such beam constitutes a circular beam that surrounds workpiece W, so that the entire surface of the workpiece is enveloped in circular arrays of light beams which strike the surface of the workpiece at different angles of incidence, again as shown by way of example by the broken lines (and arrows) in FIG. 3.

For controlling the operation of the LED's 32, it is possible selectively to energize selected groups of lamps 32 in a given ring, or various sectors of the rings R1 through R8. By way of example, each ring R1 through R8 would be divided into eight sectors with six lamps 32 in each sector. Each sector could then be selectively energized by circuit control means of the type disclosed, for example, in the above-noted U.S. Pat. No. 5,690,417, which was granted Nov. 25, 1997. That patent discloses circuit means and a controller therefor for selectively energizing LED's of the type disclosed herein, and certain of which LED's in the above-noted patent are arrayed in circular arrays, and with arcuate sectors of a respective circular array being selectively energizable by the circuitry disclosed in that patent. Accordingly, to the extent necessary to enable one skilled in the art to effect selective enerization of the LED's disclosed in this application, applicant hereby incorporates in this application the subject matter of the above-noted U.S. Pat. No. 5,690,417, and in particular the subject matter relating to FIGS. 5 and 6 of said patent.

Referring now to the embodiment shown in FIG. 4, wherein like numerals are used to employ elements similar to those disclosed in the first embodiment, numeral 50 denotes generally a modified annular lamp housing which, unlike housing 40, is truncated conical in configuration, rather than being cylindrical in configuration. Like housing 40, housing 50 is secured to and projects coaxially from the underside of housing 21 into cover 26 with the upper end thereof disposed in radially spaced relation to the optical system 22, and with the lower end thereof disposed in radially spaced relation to the opening 27 in the bottom wall 26 of housing 25. In this embodiment, however, the truncated conically shaped housing 50 has therein three-hundred-twenty, like, radial openings which are arranged in eight axially spaced rings in the housing, there being forty equi-spaced radial openings per ring. Also, while the axial centerlines of all such openings in each ring extend radailly of the axial centerline of housing 50, the centerlines of all radial openings in a respective ring lie not in a common plane that extends normal to the housing centerline, as in the first embodiment, but instead lie in a conical plane which is disposed coaxially of, and the apex of which lies on, the centerline of housing 50.

As in the first embodiment, a conventional light emitting diode (LED) 32 is secured coaxially in each of the radial openings in housing 50 and has the end thereof remote from its light emitting end extending through the outer end of a respective opening and into engagement with a truncated-conically shaped printed circuit board 54 that is secured to and surrounds the outer surface of housing 50, to supply the power for selectively energizing the lamps 32 in housing 50. As in FIG. 3 of the first embodiment, FIG. 4 illustrates only eight lamps 32 which are axially spaced from each other between the ends of housing 50, and each of which illustrated lamps is disposed in one of the eight different rings, which, as subscripts to the numerals 32 are identified as rings R1 through R8, the ring R1 being the ring of lamps which would be adjacent to the bottom of housing 21, and ring R8 being the ring of lamps being immediately adjacent to the closed end 26 of the cover 25. The light emitting ends of the lamps 32 are directed toward the axis of housing 50 with the axis of each collimated beam extending normal to the surface of the circuit board 54, and at an angle inclined to the plane of the bottom wall 26 of cover 25.

Secured to and extending coaxially between the housing 21 and the closed end of cover 25 radially inwardly of housing 50 is a truncated-conically shaped Fresnel-like diffuser element which is denoted generally by the numeral 60. Like element 40, the element 60 is made from a glass or plastic material, and has a smooth, internal bore wall 61, which is truncated conical in configuration, and which extends parallel to a conical plane containing the conically shaped lamp housing 50. In its outer peripheral surface the diffuser element 60 has formed therein a plurality of circular recesses (five in the embodiment illustrated) each of which registers with one of the rings R1 through R5 of lamps 32 in housing 50. As in the first embodiment, each of the five recesses in formed by two intersecting surfaces S1 and S2. In FIG. 4 two such surfaces in the groove which registers with the ring R2 are identified as S1 and S2, respectively; but it will be understood that each of the remaining four rings R1, R3, R4 and R5 have intersecting surfaces S1 and S2.

As in the first embodiment, the beams from each of the lamps 32 in rings R1 through R5 direct illumination onto a registering surface S2 of element 60. Also as in the first embodiment, the downward angle of inclination of the surfaces S2 increases from a minimum with respect to the surface S1 which registers with the ring R1 to a maximum for the surface S2 which forms part of the groove that registers with the ring R5. For the remainder of the element 60—i.e., the portion of its outer peripheral surface which registers with the rings R6, R7 and R8, instead of having grooves formed therein, the outer surface of element 60 has formed thereon three, nearly annular surfaces S6, S7 and S8, which register with, respectively, the rings R6, R7 and R8. With respect to an imaginary plane extending normal to the axis of the element 60, each of the surfaces S6, S7 and S8 have an angle of inclination downwardly in such plane at progressively greater values until surface S8 extends almost normal to the surface of the bottom wall 26 of the cover.

As a result of this construction, and as shown more clearly in FIG. 4, the light beams produced by the lamps 32 in the ring R8 are barely refracted, and therefore the ring of light produced thereby strikes the surface of the work W at an angle of incidence of approximately 80°. On the other hand, the light beams from lamps 32 in the ring R1 striking the uppermost surface S2 in FIG. 4 are refracted downwardly from the surface of the workpiece W at an angle of incidence of approximately 15°; and this angle increases for each successive ring of light produced by the lamps in rings R2 through R8.

From the foregoing it will be apparent that the present invention provides rather simple and inexpensive means for substantially increasing the ability of an illuminator of the type described to produce a variety of light beams having a very wide range of angles of incidence for the respective beams. While most contemporary illuminator devices of the type described have the capability of directing light beams onto a workpiece at an angle of incidence upwardly of 45°, the present invention substantially increases this range all the way from 80° down to 15°. With such a wide range, it is possible satisfactorily to illuminate the most complex of working surfaces, either by illuminating all of the LED's of a respective lamp holder 30 or 50, or selectively energizing the LED's thereof in order to illuminate selective portions of a workpiece. In this connection, while certain of the embodiments have been limited to certain numbers of rings of LED's in a respective lamp holder, and certain numbers of LED's within a respective ring, it will be apparent to one skilled in the art that the number of rings, and/or the number of lamps in a respective ring or holder can be altered without departing from this invention. Also, it will be apparent to one skilled in the art that this invention is capable of still further modification, and that this application is intended to cover any such modifications as may fall within the scope of one skilled in the art, or the appended claims.

I claim:

1. In a surface illuminator including a first housing having therein an axial bore, and a lens system in said bore adjacent one end of said housing for producing an image of an illuminated surface of a workpiece located in a predetermined position beyond and in registry with an opening formed in the opposite end of said first housing, improved means for illuminating said surface of the workpiece, comprising a second housing mounted in said first housing and having therein an axial bore disposed coaxially of an axial centerline of the bore in said first housing, a plurality of collimated light sources, each having a light emitting end, said light sources being mounted in said second housing in spaced relation to each other, and with said light emitting ends thereof facing said bore in said second housing in axially spaced circular arrays disposed coaxially of said axial centerline, each of said light sources being selectively energized to produce a collimated beam of light an axis of which intersects said axial centerline at a predetermined angle, and a generally ring-shaped lens element mounted in the bore in said second housing and coaxially of said bore, and having an outer peripheral surface confronting upon the light emitting ends of said light sources, and an inner peripheral surface disposed coaxially of said opening in said first housing, said outer peripheral surface of said element having formed thereon coaxially of said centerline a plurality of axially spaced, circumferential, light refracting surfaces each of which registers with a different circular array of said light emitting ends of said light sources to redirect beams of light from the array of light sources toward said opening in said first housing and onto said surface of the workpiece, and each of said refracting surfaces being inclined at respectively different angles with respect to said centerline, whereby said refracting surfaces direct beams of light onto the surface of said workpiece at respectively different angles of incidence.

2. The surface illuminator as defined in claim 1, wherein said refracting surfaces direct beams of light onto said workpiece surface at angles of incidence ranging from approximately 15° to 80°.

3. The surface illuminator as defined in claim 1, wherein said axis of the collimated beam of light produced by each of said light sources intersects said centerline at 90°.

4. The surface illuminator as defined in claim 3, wherein the axial bore in said second housing is cylindrical and is bound by an annular wall of said second housing, and said light sources are mounted in radial openings in said annular wall.

5. The surface illuminator as defined in claim 4, including a circuit board surrounding said second housing, and each of said light sources comprising a light emitting diode mounted in one of said radial openings in said annular wall, and having an end thereof opposite to its light emitting end electrically connected to said circuit board for selective energization thereby.

6. The surface illuminator as defined in claim 4, wherein said lens element is annular in configuration and has a smooth inner peripheral surface disposed coaxially of said opening in a bottom of said first housing, and the outer peripheral surface of said element has formed coaxially therein a plurality of axially spaced annular grooves each of which defines a pair of intersecting, circumferential surfaces on the outer peripheral surface of said lens element, and one of said circumferential surfaces of each intersecting pair thereof defines one of said refracting surfaces.

7. The surface illuminator as defined in claim 6, wherein the angles of incidence of the light beams directed onto the surface of said workpiece by said refracting surfaces range from approximately 40° to 80°.

8. The surface illuminator as defined in claim 6, wherein said second housing is generally annular in configuration and is disposed coaxially in an axial bore in said circuit board.

9. The surface illuminator as defined in claim 1, wherein said axis of the collimated beam of light produced by each of said light sources intersects said centerline at an angle inclined to a plane extending normal to said centerline.

10. The surface illuminator as defined in claim 9, wherein the axial bore in said second housing is generally truncated conical in configuration and is bound by a corespondingly shaped bore wall of said second housing, and which wall has the larger end thereof facing said opposite end of said first housing.

11. The surface illuminator as defined in claim 10, including a circuit board surrounding said second housing, and each of said light sources comprising a light emitting diode mounted in one of a plurality of spaced openings formed in said conically shaped bore wall of said second housing, and having an end thereof opposite to its light emitting end electrically connected to said circuit board for selective energization thereby.

12. The surface illuminator as defined in claim 10, wherein said lens element is truncated conical in configuration and has respectively inner and outer conical peripheral surfaces disposed coaxially of said opening in a bottom of said first housing.

13. The surface illuminator as defined in claim 12, wherein said outer conical surface of said lens element has formed therein adjacent one end thereof a plurality of axially spaced circular grooves disposed coaxially of said element, each of which grooves form one of certain of said refracting surfaces on said element, and said outer conical surface of the lens element has formed thereon adjacent its opposite end a plurality of axially spaced, circumferential surfaces inclined to each other and to said centerline and defining the remainder of said refracting surfaces.

* * * * *